United States Patent [19]
Cover et al.

[11] Patent Number: 5,702,367
[45] Date of Patent: Dec. 30, 1997

[54] RETRACTABLE-NEEDLE CANNULA INSERTION SET WITH REFINEMENTS TO BETTER CONTROL LEAKAGE, RETRACTION SPEED, AND REUSE

[75] Inventors: Walter E. Cover, Mission Viejo; Alan A. Davidner, Claremont, both of Calif.

[73] Assignee: Becton Dickinson and Company, Franklin Lakes, N.J.

[21] Appl. No.: 681,644

[22] Filed: Jul. 29, 1996

Related U.S. Application Data

[63] Continuation of Ser. No. 422,662, Apr. 10, 1995, Pat. No. 5,575,777, which is a continuation of Ser. No. 152,401, Nov. 15, 1993, abandoned.

[51] Int. Cl.$^6$ ............................................. A61M 5/50
[52] U.S. Cl. ................................. 604/110; 604/198
[58] Field of Search ............................ 604/197, 198, 604/136, 138, 230, 110, 162, 263, 194, 168, 169, 236, 190, 128, 164, 246, 247; 128/752

[56] References Cited

U.S. PATENT DOCUMENTS

| | | | |
|---|---|---|---|
| Re. 34,416 | 10/1993 | Lemieux | 604/164 |
| 2,737,950 | 3/1956 | Berthiot | 128/218 |
| 3,589,361 | 6/1971 | Loper et al. | |
| 3,938,513 | 2/1976 | Hargest | 604/190 |
| 4,391,274 | 7/1983 | Kagan | 604/190 |
| 4,512,766 | 4/1985 | Vailancourt | 604/169 |
| 4,676,783 | 6/1987 | Jagger et al. | 604/171 |
| 4,682,980 | 7/1987 | Suzuki | 604/122 |
| 4,747,831 | 5/1988 | Kulli | 604/110 |
| 4,762,516 | 8/1988 | Luther et al. | 604/164 |
| 4,772,265 | 9/1988 | Walter | 604/164 |
| 4,781,692 | 11/1988 | Jagger et al. | 604/164 |
| 4,828,548 | 5/1989 | Walter | 604/164 |
| 4,832,696 | 5/1989 | Luther et al. | 604/164 |
| 4,838,869 | 6/1989 | Allard et al. | 604/195 |
| 4,900,307 | 2/1990 | Kulli | 604/110 |
| 4,904,242 | 2/1990 | Kulli | 604/110 |
| 4,909,793 | 3/1990 | Vining et al. | 604/164 |
| 4,917,671 | 4/1990 | Chang | 604/168 |
| 4,936,830 | 6/1990 | Verlier | 604/110 |
| 4,950,252 | 8/1990 | Luther et al. | 604/198 |
| 4,978,343 | 12/1990 | Dysarz et al. | 604/195 |
| 4,978,344 | 12/1990 | Dombrowski et al. | 604/198 |
| 5,013,304 | 5/1991 | Russell et al. | 604/167 |
| 5,125,414 | 6/1992 | Dysarz | 128/763 |
| 5,129,884 | 7/1992 | Dysarz | 604/164 |
| 5,273,540 | 12/1993 | Luther et al. | 604/110 |
| 5,330,443 | 7/1994 | Powles et al. | 604/240 |
| 5,346,480 | 9/1994 | Hess et al. | 604/197 |
| 5,395,342 | 3/1995 | Yoon | 604/167 |
| 5,501,671 | 3/1996 | Rosen et al. | 604/168 |

*Primary Examiner*—Michael Powell Buiz
*Assistant Examiner*—At Nguyen
*Attorney, Agent, or Firm*—Eric M. Lee

[57] ABSTRACT

Leakage of blood from the insertion set, during and after safety-needle retraction, is suppressed by components that receive and retain flash blood for viewing—notwithstanding forces developed within the device in retraction. One preferred such system includes a flash chamber that moves with the retracting needle, within a hollow handle, carrying a relatively high flow-impedance element which allows air exhaust from the chamber into the handle to admit flash blood—but isolates blood in the chamber from retraction-generated increase in air pressure in the handle. Energy-absorbing components control or compensate for retraction speed, to provide quiet smooth retraction—while yet enabling use of ample retraction force to make retraction reliable. Among several energy absorbing systems disclosed is a preferred one that includes a viscous material introduced within the hollow handle to damp the retracting motion; and an injection port to facilitate introduction of the viscous material. Needle reuse, and concomitant risk of spreading disease, are avoided through components that deter needle redeployment—by deterring access to or forward motion of the needle, or trigger reengagement.

5 Claims, 7 Drawing Sheets

RETRACTABLE-NEEDLE CANNULA INSERTION SET WITH REFINEMENTS TO BETTER CONTROL LEAKAGE, RETRACTION SPEED, AND REUSE

This is a continuation of application Ser. No. 08/422,662, now U.S. Pat. No. 5,575,777, filed Apr. 10, 1995 which is a continuation of application Ser. No. 08/152,401, now abandoned, filed Nov. 15, 1993.

BACKGROUND

1. Field of the Invention

This invention relates generally to medical appliances; and more particularly to a device for inserting into a patient's body a medical appliance such as a cannula, e.g., an intravascular cannula, or such as a guidewire used for emplacing catheters etc. The invention is for helping protect people from contracting diseases (particularly fatal diseases such as AIDS and hepatitis) through accidental puncture by needles that have been used in diseased patients.

2. Prior Art

U.S. Pat. No. 4,747,831 to Kulli sets forth the state of the pertinent art and is, in its entirety, incorporated herein by reference. Kulli teaches a safety device for use in inserting a cannula into a patient and for thereafter protecting people from contact with portions of the device that have been within the patient.

(For purposes of this document as in the Kulli patent, the term "cannula" means a catheter assembly consisting of primarily a hub and short tube—as pictured and described in the Kulli patent [column 3, lines 25 through 37] and herein. As already mentioned the technology is not necessarily limited to use with cannulae directly but is useful as well in insertion of other medical appliances such as catheter guidewires.)

Kulli's device includes a needle for piercing a patient and for guiding and carrying a cannula or other appliance into place within such a patient; the needle has a shaft with at least one sharp end. His device also includes a hollow handle adapted to enclose at least the sharp end of the needle beyond reach of people's fingers.

In one major facet or aspect of preferred embodiments of Kulli's invention, the invention also includes some means (denominated the "securing means") for securing the shaft to the handle, with the sharp end projecting from the handle. It also includes some means (the "releasing means") for releasing the securing means and for substantially permanently retracting the sharp end of the needle into the handle and beyond reach of people's fingers. The releasing and retracting means are manually actuable by a simple unitary motion, of amplitude that is substantially shorter than the shaft of the needle.

In a second major aspect or facet, Kulli's invention also includes (in addition to the needle and hollow handle) a block fixed to and extending from the needle. The block is restrained within the handle with the sharp end of the needle projecting out of the handle through the aperture, and adapted for motion within the handle to withdraw the needle into the handle. The invention in this second major aspect further includes a trigger mechanism, which is actuable from outside the handle for releasing the block. The trigger mechanism also includes positive biasing means for forcibly moving the block within the handle to substantially permanently retract the sharp end of the needle into the handle and beyond reach of people's fingers.

Many other details of the Kulli invention are discussed at length in his '831 patent and for economy's sake will not be repeated directly here, though as already noted they are all incorporated into this document by reference.

In the course of very extensive efforts directed toward preparation of the Kulli invention for the marketplace, it has been confirmed that his invention is entirely operational and serviceable for all the purposes described. No criticism of the structure or function of Kulli's invention is intended by, and none should be inferred from, anything in the present document.

To enhance acceptance of such a device by the medical community and regulatory authorities, it has been found desirable to focus attention upon certain operating characteristics of the Kulli device—particularly as they relate to peripheral but very important matters. Such matters include (1) manufacturing economics, and possible resulting variations in operation, (2) variations in skill of—and consequently variations in handling by—operating personnel, and resulting perceptions of medical appliances by operating personnel, and (3) potential misuse of the device, due for example to prevailing societal conditions.

It will now be understood that none of these considerations can properly be regarded as in the nature of a defect or limitation of Kulli's invention. Rather they are in the nature of areas in which that invention leaves room for further refinement.

None of these considerations is, in substance, a part of the prior art; instead they have been adduced through work leading to the present invention, and are regarded as at least in part components of the creative and innovative processes of making the present invention. Accordingly in this document these considerations will be detailed in a later section, not addressed to the prior art.

For reference purposes, however, the present section will now describe the overall procedure for inserting a cannula or the like—whether using the Kulli device or essentially any other cannula insertion set—as this procedure itself is a part of the prior art and will be of interest in later discussion of the present invention. Typically a doctor, nurse, paramedic or other medical staff person first locates a target blood vessel chosen for catheter insertion, and then pierces the patient's skin and blood-vessel wall—inserting the pointed end of the needle and a portion of the catheter (see FIG. 16 of Kulli).

Next the practitioner almost always deliberately permits a small quantity of the patient's blood to flow through the hollow needle—impelled by the patient's own blood pressure—so that the small quantity of blood can be seen at the rear of the needle. The blood which thus flows from the needle enters some sort of chamber that is part of the cannula insertion set, and which ordinarily is made of transparent material to afford a view of the interior and thus of the blood therein.

This practice of allowing some blood to flow into a viewing chamber is known in jargon of the medical field as "flashing", and the blood that enters the chamber is sometimes called the "flash" quantity. The flashing step has the purpose of confirming that the catheter is indeed inserted into the blood vessel.

In the instance of Kulli's invention, the chamber is the hollow handle into which the needle will later be retracted, and which thus serves double duty as a viewing chamber.

In other types of cannula insertion sets too the chamber may be a hollow handle, but may take other forms. In such other types of sets, the chamber is generally configured in one way or another to permit the flash blood to enter the chamber—but then to retain that blood.

To permit entry of that blood into the solid chamber, some provision must be made for escape of air that is initially in the chamber; on the other hand, retention of the blood once it has entered the chamber requires that the chamber be to some extent fluid sealed. These two seemingly contradictory requirements can be and are satisfied in a variety of ways, including careful placement of breather holes or tubes to permit air escape—and so accommodate the slow passage of blood into the chamber—while presenting a relatively long, high-impedance path to obstruct liquid flow out of the chamber.

More often modernly these requirements are met by providing—for instance at the rear end of the handle—a relatively large orifice that is closed by a selective filter to pass air somewhat readily, at least at the flow rates typically associated with blood flow into the chamber, but block passage of blood out of the chamber. As will be understood such purposes may be best served by for example a hydrophilic filter; such filters are sometimes used.

Once a desired flash quantity of blood is observed, as mentioned in the Kulli patent the medical practitioner usually provides temporary stoppage of the blood flow by placing a finger or other hand portion upon the blood vessel to squeeze off the vessel. While maintaining this stoppage the practitioner carefully withdraws the needle, leaving the inserted end of the cannula or other appliance in place—and then secures an appropriate intravascular connecting tube, most typically a delivery tube, to the hub of the cannula etc.

Next the practitioner fixes the cannula or like appliance to the patient's body, usually employing a small piece of tape, and releases the manually applied closing pressure upon the vessel. Various liquids may then be introduced through the appliance into the patient's blood stream, the patient's blood pressure may be monitored, etc., all as well known.

Also part of the prior art are teachings of certain other Kulli patents, including U.S. Pat. Nos. 4,900,307, 4,904,242, 4,927,414 and 4,929,241—some of which disclose features related to deterrence of needle reuse, but in different contexts.

Important aspects of the technology used in the field of the invention are amenable to useful refinement.

SUMMARY OF THE DISCLOSURE

The present invention introduces such refinement. Before offering a relatively rigorous discussion of the present invention, some informal orientation will be provided here.

It is to be understood that these first comments are not intended as a statement of the invention. They are simply in the nature of insights that will be helpful in recognizing the underlying character of the special considerations alluded to above (such insights are considered to be a part of the inventive contribution associated with the present invention) —or in comprehending the underlying principles upon which the invention is based.

Flash leakage—Through extensive work with devices constructed according to Kulli's disclosure, it has been discovered for example that some personnel sometimes handle the devices in such a way that blood from a patient can leak rearward or forward from the handle of the device, or forward from the needle. Some of the procedures leading to such leakage are necessary parts of the usage of the device—detailed in the preceding section of this document—and others are in the nature of variations in operator skill, attentiveness or anticipation, and the like.

In any event, for success of a device to be used in very large numbers throughout the medical industry it is highly desirable to minimize the potentiality for blood leakage resulting from such handling variations. The portion of procedures that sometimes leads to blood leakage is the so-called flashing step already described in the previous section of this document.

At the outset it may be noted that the Kulli disclosure does not propose to position a filter over the rearward orifice 13 etc. of the hollow handle, or otherwise to provide for selective passage of air but not blood as in some other insertion devices. Kulli instead proposes that the rearward orifice 13 etc. may be preserved open and at substantially the same internal diameter as the cannula hub—thus making possible a temporary attachment of intravascular tubing through the handle, as is sometimes desired by some medical professionals, preparatory to shifting the attachment to the cannula hub.

In the present state of medical practice, however, such temporary attachments are disfavored and retention of the flash blood is regarded as more important. It might be supposed accordingly that the Kulli device should simply be fitted with a suitable filter at its rear orifice 13 etc.—or that the rear orifice should be eliminated by sealing the rearward end of the handle and some other provision (e.g., small vent holes or tubes) incorporated for escape of air to accommodate incoming flash blood.

In efforts toward resolving this consideration, however, it was learned with some surprise that such emplacement of a filter or a fine vent was not sufficient. The reason is that the retraction of Kulli's needle, or needle and block, into the hollow handle tends to displace a volume of flash blood collected in the handle. This displacement tends to expel blood abruptly out of the enclosure by whatever path is available.

One leakage path is forward through the needle and its carrier block. In other words, in such a device when the retraction button is operated blood can be squirted out of the front end of the needle—an unacceptable result, not merely because of the untidiness involved but more importantly on account of the exposure of people in the vicinity to the patient's blood. The latter is particularly troublesome since an important objective in providing a retracting needle is to minimize such exposure.

Another path—once the needle carrier block has retracted out of its initial or forward-locked rest position with minimal radial clearance—is forward around the needle and block. In this instance the blood leaks out of the assembly by issuing through the forward apertures of the Kulli handle or housing.

This path, utilizing only incidental clearances in the apparatus, tends to create smaller leakage than that through the needle—particularly with respect to the immediate, piston-driven expulsion of blood at the time of retraction. This second path, however, remains important because of a potential for somewhat slower but more protracted trickling of blood from the front of the chamber, sometimes occurring after use of the device is nominally complete and it has been laid down on a table or tray—so that personnel may no longer be attentive to the possibility of blood leakage.

Further, in the course of development, it was noted that the possibility of abrupt expulsion of blood through the needle was reduced very greatly through fabrication of the needle carrier block with relatively greater radial clearance—and by instructing medical personnel not to fill the handle more than about three-quarters full. These two provisions, coupled with the relatively high viscosity of blood in the needle, allowed enough mechanical volume for rearrangement of the blood within the chamber, upon retraction, and thereby nearly eliminated the squirting of blood through the needle.

In some cases, however, it is not possible to avoid filling the chamber beyond the three-quarters point; with patients who have large blood vessels and high blood pressure, for example, the chamber may be filled with flash blood very quickly. It was found that highly skilled and specially instructed personnel could reliably avoid overfilling, by anticipating rapid filling in appropriate cases, and by particularly dextrous manipulations; but in general use the volumetric suitability of the flash is simply outside the control of the insertion-set manufacturer.

Furthermore, providing a relatively high clearance around the needle block—while reducing the potentiality for abrupt expulsion of blood through the needle—has the undesirable effect of aggravating the potentiality for longer-term leakage of blood along the incidental clearances around the needle. Efforts to resolve the latter complication through incorporation of a specially sized resilient seal at the forward end of the device were operationally successful but objectionably expensive, and in particular also objectionably cumbersome in assembly—and as will be understood could not address the former matter of flash-volume control.

As can now be appreciated, the seemingly simple initial expedient of providing a substantially conventional flash-chamber enclosure for the Kulli device—as by placing a filter at the rear aperture of that unit, or by otherwise closing that orifice and incorporating vents—can lead to blood expulsion or leakage concerns of magnitude at least equal to the initial desire to enclose the flash.

Only after very extensive experimentation and trial-and-error efforts was it realized that the source of this concern is the implicit initial choice of enclosing or barring the flash blood at a point that is fixed relative to the handle. This choice in turn implies relative motion between that blood, in the handle, and the piston formed by the moving needle block.

It is this relative motion, particularly motion of the carrier block moving through the blood, which causes the primary concern over leakage—that is, the abrupt expulsion of blood forward through the needle. Accordingly a resolution of this concern can be sought in the alternative of enclosing or barring the flash blood at a point that is effectively fixed relative to, instead, the movable needle—thereby enabling elimination of effective relative motion between the blood and the moving needle block.

The words "effectively" and "effective" have been used above because, as will be seen, some configurations that prevent application of retraction forces to the flash blood involve pneumatic association of the blood enclosure with the moving needle even though the enclosure may be fixed to the handle.

As will be seen, this change of focus opens a variety of possibilities for allowing air to escape from the enclosure so that flash blood can flow from the rear of the needle—and for then holding the blood safely enclosed even during needle retraction. In particular, in such a configuration a filter or vent too can be associated with the moving needle.

That association yields the beneficial result that the limited airflow capacity of the filter or vent (relative to air moved by the piston effect during retraction) now works favorably toward leak-free operation. The limited-airflow filter or vent does so by isolating the flash blood in the chamber against the air-pressure increase developed in retraction.

Hence the moving needle, carrier block, chamber, filter or vent, and flash blood all together form and act as a composite piston upon the air in the hollow handle. Furthermore the handle itself no longer need be sealed by a filter or fine vent, and the air moved by the composite piston can be rapidly relieved to ambient.

Still another alternative for resolving leakage concerns can be found in the isolation of flash blood in the needle (as distinguished from the receiving chamber) from air-pressure increases developed in retraction. A check valve, for example, can be provided to perform this function.

Retraction speed—Retraction of the Kulli needle and block are, in some preferred embodiments, effectuated by a biasing means such as for example a coil spring. Whatever propulsion unit is used, the resulting retraction speed is subject to variations in biasing force—which are compounded by variations due to dimensional tolerances for the needle, block and handle; and particularly by highly variable lateral and torsional forces developed on the needle tip, as for example by the manual pressure mentioned earlier.

These factors together create a very large range of variation in the final resultant retraction speed. In consequence, if the various tolerances are chosen to be substantially certain of positive and prompt retraction when all factors tend toward minimum retraction force and speed, then objectionably high speed results when all factors tend toward maximum force and speed.

Retraction speed may be objectionably high even though the mechanism functions perfectly and poses no threat of injury or damage—either to itself or to anything else. The objectionability of high speed arises rather from the perceptions of some medical personnel, for whom unusually forcible or loud retraction may be startling or annoying, or simply may seem unprofessional.

It will be understood that a high range of variation in speeds—leading, as explained above, to quite high speed in some cases—can be avoided by constraining mechanical tolerances more closely. Such resort to tighter specifications, however, is itself objectionable on account of the associated higher cost.

As implied already, objectionably high speeds and consequent loud clicking or snapping sounds can be avoided by using lower spring pressure, closer clearances, etc.—but not without shifting the problem to the low-speed end of the overall range of variations, or in other words causing some needles to retract unreliably or too slowly.

Part of the present invention accordingly resides in recognition that retraction can be both (1) made reliable and (2) controlled in speed—but within a very economical device—by in essence assigning these two functions to two different mechanical elements respectively. More specifically, positive and prompt retraction can be assured by selecting a sufficiently strong spring or other biasing means; and it is possible to prevent or compensate for excessive retraction speed by incorporating a damping or other energy-absorbing provision.

A suitable energy-absorbing element can for instance take the form of a viscous lubricant interposed between the needle carrier block and the interior bore of the hollow handle; and means (such as a lubricating port) for facilitating placement of the lubricant. This type of energy-absorbing provision may not provide a resistive force that is consistent over the full travel of the needle; rather the consequent speed-limiting action appears to be concentrated at the beginning of the stroke and may result in part from thixotropic or stiction-like effects.

Such effects may include, for example, (1) a tendency of the lubricant to make spring coils stick together, and for the spring coils to break loose only gradually to begin the stroke, and similarly (2) a tendency for the lubricant to make the needle carrier block stick in place against the interior bore of the handle, and for the block to break loose from the bore surface only gradually at first. In any event, whether or not the operative mechanisms of the technique are fully understood at a physics or classical-mechanics level, this form of energy absorbing has been found very satisfactory.

This type of energy absorbing also offers an additional benefit of sealing the carrier block against the interior bore, before the needle is retracted. Under these conditions suction (e.g., from an external plunger), can be applied to the interior passage, and thereby to the flash chamber and needle lumen, to assist in drawing flash blood into the chamber. Such a suction boost is desirable to assist in the flashing procedure on some occasions, as when for instance the patient's blood pressure is very low.

Other energy-absorbing elements, however, are believed to be usable and within the scope of the invention. For example a separate mechanical element can be disposed within the hollow handle and biased laterally (e.g., radially) against the needle or carrier block to impose frictional force tending to retard the retraction; in such a system, biasing force and surface materials are selectable to obtain desired damping levels. In such a configuration the biasing force may preferably be varied along the stroke—as for example by using or exaggerating the draft generally employed in molding of hollow shapes such as a handle housing.

As another example, a dashpot device may be formed by separate or preferably existing elements within the hollow handle. In this case the energy-absorbing effect would appear to be more in the nature of true damping than the viscous-lubricant system, but may tend to be concentrated near the end of the retraction stroke, whereas in the case of the preferred viscous-lubricant technique the damping action tends to be concentrated near the beginning of the retraction stroke.

Risk of Abuse—Unfortunately in present-day society a widespread phenomenon is use of discarded medical needles by drug addicts to inject themselves with hallucinogenic drugs and the like. Apart from the social evils of addiction and resulting crime, such abuse of discarded medical equipment poses a risk of spreading disease from the blood of diseased patients.

Thus in addition to its primary function of deterring the inadvertent infection of medical personnel through accidental needle punctures, it is desirable that any disposable medical appliances which include needles be configured to deter or discourage later reuse.

Study of the '831 patent suggests that the needle and its carrier block might be reset forward within the handle by insertion of an elongated tool such as a screwdriver blade, to push against the rear end of the needle or block. While the block and needle are thus held in a forward position, they can once again be locked in that position by resetting the latch button outward.

Alternatively, even a relatively short tool may be used to start the sharp needle tip back through the forward end of the handle. A person may thereby be enabled to grasp the tip with fingers, pliers or the like and pull it forward to complete the forward-resetting motion.

In either of these ways a person may be able to fully or partially redeploy—and thereby prepare to abuse— potentially contaminated medical needles following their disposal by hospitals and other medical facilities.

Such abuses can be frustrated by configurations that obstruct or otherwise deter insertion of such tools. As will be understood, virtually nothing can be done to prevent a person from cutting open the rear end of the handle to gain unobstructed access to the needle within; short of such tactics, however, as will be seen a variety of abuse-frustrating configurations is within the scope of the invention.

Now with these preliminary observations in mind this discussion will proceed to a perhaps more-formal summary. The invention has several major aspects or facets.

In preferred embodiments of a first of these primary aspects, the present invention is a safety device for use in inserting a medical appliance such as a cannula into a patient and for thereafter protecting people from contact with portions of the device that have been within the patient—and from contact with the patient's blood. The device includes a hollow needle for piercing a patient and for guiding and carrying such an appliance into place within the patient; the needle has a shaft with at least one sharp end;

The device of the first aspect of the invention also includes a hollow handle adapted to enclose at least the sharp end of the needle beyond reach of such people's fingers; and some means for securing the shaft to the handle, with the sharp end projecting from the handle. These means, for purposes of breadth and generality in discussion of the invention, will be called the "securing means".

The device further includes some means for releasing the securing means and for substantially permanently retracting the sharp end of the needle into the handle and beyond the reach of such people's fingers. These means, again for generality and breadth, will be called the "releasing and retracting means"; they are manually actuable by a simple unitary motion, of amplitude that is substantially shorter than the shaft of the needle.

The device also includes some means for receiving blood from within the hollow needle and for reliably retaining that blood during and after retracting of the needle, notwithstanding forces developed by the retracting.

The foregoing may represent a description or definition of the first main facet of the invention in its broadest or most general form. (A considerable variety of different kinds of receiving and retaining means is introduced elsewhere in this document.)

Even in this form, however, this first aspect of the invention may be seen to provide the refinement needed to resolve concerns discussed earlier in this section of the present document. In particular, because the receiving and retaining means accept and hold the blood even in the face of retraction forces, they make possible avoidance of the flash expulsion sometimes observed upon fitting Kulli-type devices with a selective filter.

Nevertheless, for greatest enjoyment of the benefits of the invention, it is considered preferable to practice this first broad aspect of the invention in conjunction with certain other characteristics or features. It is particularly preferable to practice this first main facet of the invention in conjunction with the other principal aspects, to be introduced below; however, in addition to those major aspects there are several other preferable features or characteristics.

For example, the receiving and retaining means most preferably comprise a chamber fixed for motion with the needle; and some means for permitting viewing of received and retained blood by a user of the device. More specifically, it is preferred that the chamber be fixed to the needle, within the hollow handle.

It is also preferred that the receiving and retaining means further comprise some means for isolating the interior of the chamber from forces developed by said retracting. Several such isolating means are within the scope of the invention.

Among these are systems that include relatively high-impedance means for transmitting gas from the interior of the chamber. Such systems may for instance include means for permitting relatively slow escape of air from the interior of the chamber to enable entry of blood through the hollow needle; and means for deterring relatively rapid entry of air into the interior of the chamber to avoid expulsion of blood through the hollow needle by forces developed in retracting. Such high-impedance transmitting means may take the form of a selective filter, or a fine passage for venting air.

Alternatively, the receiving and retaining means preferably may include a chamber associated with the handle; and some means for transmitting blood from within the hollow needle into the chamber, substantially without transmitting into the chamber force developed during said retracting. For example blood-transmitting means may include a flexible tube communicating between the chamber and the interior of the hollow needle; or a frangible passage communicating between the interior of the chamber and the interior of the hollow needle (in which system the releasing and retracting means break the frangible passage); or a check valve disposed along a blood-flow path between the interior of the chamber and the interior of the hollow needle.

In preferred embodiments of a second major facet or aspect of the invention too, the invention is a safety device for use in inserting a medical appliance such as a cannula into a patient and for thereafter protecting people from contact with portions of the device that have been within the patient. This device too includes a hollow needle, hollow handle, securing means, and releasing and retracting means manually actuable by a simple unitary motion, of amplitude substantially shorter than the shaft of the needle—all substantially as set forth above.

In addition a device according to preferred embodiments of this second major facet of the invention also includes some means for absorbing some of the energy of the retracting—which will be denominated, for purposes mentioned earlier, "energy-absorbing means" or simply "absorbing means". (A variety of absorbing means may be employed, within the scope of the invention, as set forth elsewhere in this document.)

While the foregoing may represent a definition or discussion of the second aspect of the invention in its most general or broad form, once again this aspect too can be seen to resolve concerns discussed earlier in this section. In particular the energy-absorbing means enable the needle carriage to be amply powered for reliable retraction, since so powering the carriage no longer need produce objectionably loud, or startling retraction sounds—or objectionably forcible or jerky operation.

Nevertheless it is preferable, to maximize the benefits of the invention, that this second main facet of the invention too be practiced in conjunction with certain other features and characteristics that enhance its advantages. For example it is preferred that the device also include some biasing means for powering the retracting reliably, despite accumulated manufacturing tolerances tending against said retracting—or, in other words, that the possibility mentioned in the preceding paragraph be actualized by providing ample retraction force.

It is also preferred that the absorbing means include a viscous substance interposed between the needle and the hollow handle; and further that these means include a port defined in the hollow handle for placement of the viscous substance within the hollow handle.

Alternatively the absorbing means preferably include a surface that is fixed to one of (1) the needle and (2) an interior bore of the handle; and an element carried on the other of the needle and that interior bore, and bearing against said surface to develop friction during said retracting. Still further alternatively the absorbing means preferably include a dashpot element fixed for motion with the needle in said retracting.

In preferred embodiments of a third of its main facets or aspects, the invention is as before a safety device for use in inserting a medical appliance such as a cannula into a patient and thereafter protecting people from contact with portions that have been within the patient. This device includes as before a hollow needle, hollow handle, securing means, and manually actuable releasing and retracting means as characterized earlier.

In addition a device according to this third main facet of the invention includes some means—the "deterring means"—for deterring redeployment of the needle after said retracting. (A number of different forms of such means are described elsewhere herein.)

The foregoing may constitute a definition or description of this third aspect of the invention in its broadest or most general form. Even in this broad form, however, it may be seen to resolve needle-abuse concerns mentioned earlier in this section, as the deterring means will significantly reduce the risk of needle reuse by addicts and others, thereby correspondingly reducing the risk of disease propagation through such abuse.

Nevertheless this third facet of the invention, to optimize the benefits which it provides, is preferably practiced in conjunction with certain other features or characteristics. For example it is preferred that the deterring means deter access to the needle after said retracting. Also it is preferred that after the retracting the deterring means alternatively or additionally deter forward movement of the needle, or reengagement of the securing means, or both.

In preferred embodiments of a fourth major aspect of the invention, the invention is a catheter-insertion device with a retracting needle, and includes an elongated hollow needle having a piercing end and an interior end. The device also includes a handle defining an interior passage.

In addition this device includes a needle carriage, movably received within the interior passage, defining an interior chamber and supporting the needle so that the interior end of the needle communicates with the interior chamber and the piercing end of the needle extends outward. The device also includes some means for securing the needle and carriage with the piercing end of the needle outside the handle. In addition the device includes some means for releasing the securing means and retracting the needle and carriage inward with respect to the handle so that the piercing end of the needle is inside the handle.

The foregoing may represent a definition or description of the broadest or most general form of the fourth primary facet of the invention. Once again the invention in this form will be seen to resolve important concerns of abrupt leakage or squirting of blood, which arise upon fitting a Kulli device with a selective filter as described earlier in this section.

The invention as broadly couched in this fourth main aspect resolves such concerns by carrying the blood with the needle during retraction, rather than holding the blood in the handle—so that there is no relative motion between the blood and the needle. Under these conditions it remains only to deal with the compressive forces developed during retraction, to prevent application those forces to the blood that is carried with the needle; dealing with those forces can be accomplished by various means as indicated elsewhere in this document.

Nevertheless it remains preferable to practice this fourth major aspect of the invention in conjunction with other features or characteristics that lead to the most advantageous overall structure and function. For example it is preferred that the interior chamber include some means for making visible any contents of the interior chamber.

In addition preferably the interior chamber defines a first end sealingly attached to the interior end of the needle, and a second end. Preferably the needle carriage further includes means for permitting slow passage of air, and for deterring passage of blood, outward from the interior chamber into the interior passage of the handle; and for deterring rapid passage of air inward into the interior chamber from the interior passage of the handle.

These permitting-and-deterring means preferably comprise a filter covering the second end. Such a filter is preferably of a hydrophilic material.

Also preferably the handle defines an injection aperture for introducing a viscous substance into the interior passage of the handle; and the device further includes a viscous substance introduced through the injection aperture and disposed between the carriage and an interior surface of the handle. In addition preferably the device includes a grill secured across the interior passage of the handle.

As mentioned earlier it is preferred that all these major facets or aspects of the invention be practiced in conjunction with one another. They are all, however, to various extents capable of practice independently.

All of the foregoing operational principles and advantages of the present invention will be more fully appreciated upon consideration of the following detailed description, with reference to the appended drawings, of which:

DETAILED DESCRIPTION OF THE PREFERRED EMBODIMENTS

Figure 1:
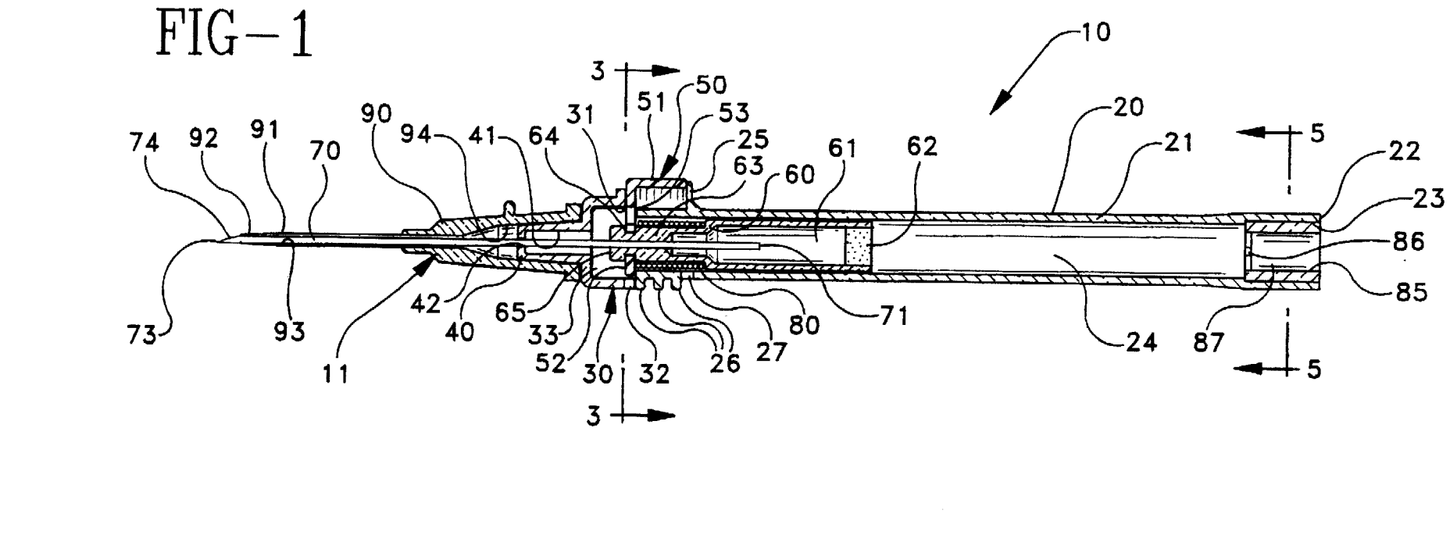
FIG. 1 is a longitudinal section of a retracting-needle cannula-insertion device according to preferred embodiments of the invention—using for pressure isolation a flash chamber that moves with the needle, and for energy absorbing a viscous substance and a port for positioning the substance—shown together with a cannula that can be inserted using the device, and particularly showing the needle in its extended position.
Figure 3:
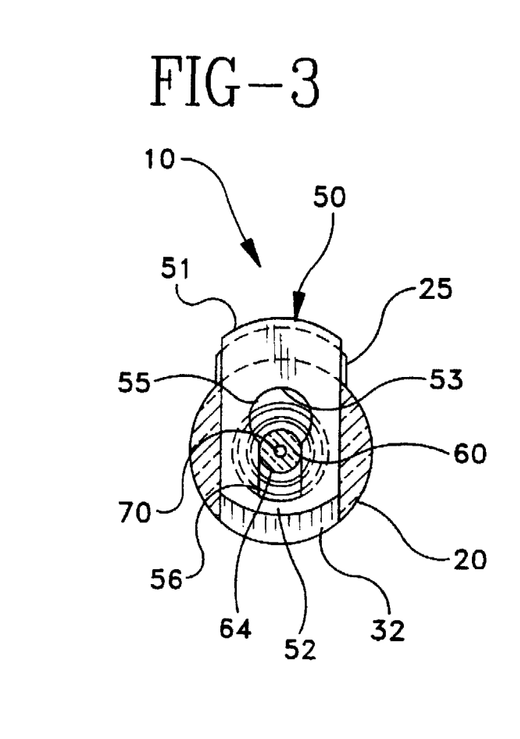
FIG. 3 is a cross-section of the same device taken along the lines 3—3 of FIG. 1 and so showing the needle extended.

FIGS. 1 and 3 show a preferred embodiment 10 of the invention, having an elongated generally cylindrical handle housing 20 with a cylindrical wall 21 and a cylindrical interior passage 24. The housing 20 also defines an end portion 22 with an increased-diameter end recess 23.

A cylindrical end plug 85 defines an air passage 87 and a grill 86, which may by way of example be cruciform as shown. This plug 85 is secured within the end recess 23 using a force or interference fit, together with other appropriate attachment provision such as, for instance, adhesive or sonic welding.

Formed in an outer surface of the handle housing 20 is a radially extending (or upward-extending, with the device oriented as drawn in FIG. 1) trigger guard 25, and a plurality of ribs 26 to facilitate positive grasping of the device by a user. Also formed in the handle housing, through the cylindrical wall 21 for communication with the cylindrical interior passage 24, is a generally circular grease port 27.

A frontal housing 30 is secured to the forward end of the handle housing 20—again by any appropriate means such as adhesive, sonic welding etc., but preferably by a snap fit—and defines a generally tapered forward-extending nose portion 40, with a needle-passing aperture 42 formed at the forwardmost tip, and a tapered passage 41 generally coextensive with the nose portion 40 and communicating between the interior cavity 33 of the frontal housing and the needle aperture 42.

Formed transversely through either the frontal housing 30 or the front end of the handle housing 20—but preferably through the latter—is a pair of opposed slots 31, 32. A lock slider or trigger 50 (to some extent better seen in FIGS. 3 and 4) defines an elongated generally planar lock member 52—preferably formed of a strong material such as metal, and slidably received through the opposed slots 31 and 32. Formed through the planar lock member 52 is a keyhole-shaped aperture or slot 53.

Movably and preferably slidably received within the cylindrical interior passage 24 of the handle is a carriage or carrier block 60. This carriage 60 in turn defines an interior flash chamber 61, and a reduced-diameter portion 63.

Extending through and secured within this latter portion 63 of the carriage 60 in a sealed attachment is an elongated hollow needle 70. An internal end 71 of the needle 70 is positioned in communication with and preferably within the interior flash chamber 61.

The remainder of the hollow needle 70 extends forward from the carriage 60—through the tapered passage 41 and aperture 42 in the nose portion 40 of the frontal housing 30, and beyond. The needle terminates in a piercing point formed by a beveled facet 74.

Thus flash blood passing from a patient into the device through the hollow needle 70 is introduced into the interior flash chamber 61 for viewing. The device includes some means for permitting viewing of the flash blood by a user of the device; such means may include a separately defined transparent window, but preferably they include transparent materials used in fabrication of the entire chamber 61, indeed the entire carriage 60—as well as the handle housing 20.

The needle carriage 60 also defines a front end 65, a circumferential, preferably circular groove 64, and a rear end that is spanned by a hydrophilic filter 62. (Hydrophobic/hydrophilic composite units are also potentially useful.) This filter provides liquid sealing of the flash chamber 61 while permitting outward air diffusion into the passage 24 of the handle.

A coil spring 80 encircles and receives the reduced diameter portion 63 of the needle carriage 60, and is captured between the needle carriage 60 and, for convenience, the lock slider 50. As will be clear, the spring 80 can as well seat against an internal feature of the handle.

A conventional catheter or cannula 11 includes a catheter housing 90, with an interior cavity 94 that receives the nose portion 40 of the frontal housing 30 in a conventional attachment such as preferably a snap fit. (Description of the invention here in conjunction with a cannula is only for definiteness of description; as mentioned earlier the invention is for emplacement of other medical appliances as well.) The cannula 11 also includes an elongated hollow catheter tube 91 with an end portion 92—and a needle passage 93 formed through the tube 91 and end portion 92.

The interior end of the catheter tube 91 is sealingly secured, as is conventional, within the interior cavity 94 of the catheter housing 90. In the assembled position of FIG. 1, the piercing point 73 and bevel 74 of the needle 70 extend slightly beyond the end 92 of the catheter tube 91 to facilitate the piercing action of the needle unit 10.

FIG. 1 represents the needle-extended condition of the device, in which the carriage 60 and needle 70 have been drawn forward against the force of the compressing spring 80—so that the groove 64 in the front end 65 of the carriage 60 is aligned with the keyhole aperture 53 in the slider/trigger 50—and are held in that forward position by the slider 50.

This forward positioning of the needle 70 and carriage 60 is accomplished while the trigger 50 is initially moved downward (as drawn) within the slots 31, 32 of the frontal housing 30 or handle 20, thereby aligning the larger-transverse-dimension, circular part 55 (better seen in FIG. 4) of the keyhole aperture 53 with the end portion 65 of the needle carriage 60. The end portion 65 has then been passed through the larger-transverse-dimension circular part 55 of the keyhole, just enough to align the circumferential groove 64 in the carriage 60 with the planar trigger plate 50.

With the carriage 60 thus longitudinally aligned, the lock slider 50 has been raised (as drawn) to the position shown in FIGS. 1 and 3 so that the narrower portion 56 of its keyhole-shaped aperture 53 is fitted into the carriage groove 64, capturing and holding the carriage 60 and needle 70 in their forward positions—against the force of the spring 80. At this stage, the device 10 with associated cannula 11 is ready for use.

Now in proper use a medical professional manipulates the device 10, holding it by the handle housing 20, to pierce the patient's skin and target-vessel wall—and thereby insert the piercing point 73 and cannula tip 90 into the target vessel. Once this occurs, a small volume of the patient's blood, the flash blood, is forced through the passage of the hollow needle 70 by the patient's blood pressure and flows into the flash chamber 61—readily expelling before it from the chamber a like volume of air, through the filter 62.

The blood itself, however, is substantially obstructed by the filter and so is substantially completely confined within the chamber 61, where the blood may be readily observed to confirm proper insertion of the needle and catheter. Once the flash blood has been observed, the medical practitioner then withdraws the needle 70 from the patient's body while maintaining the cannula 11 in place.

At this juncture the device 10 contains a quantity of the patient's blood within the flash chamber 61, and the needle 70—both externally and within its hollow passage—is contaminated with a small quantity of the patient's blood. Thus in accordance with preferred safety practice the device 10 should be discarded with due care for the possibility of infecting people with that blood.

Figure 2:
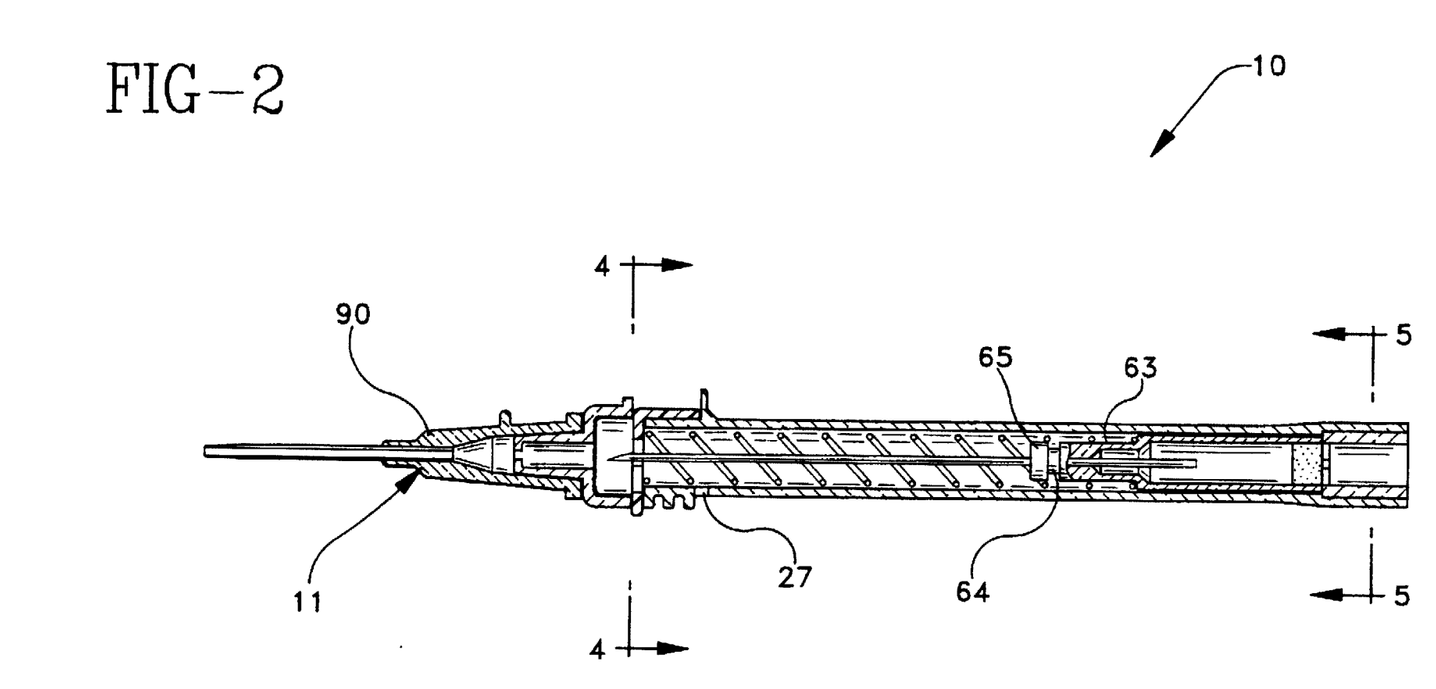
FIG. 2 is a like view of the FIG. 1 device but showing the needle retracted.
Figure 4:
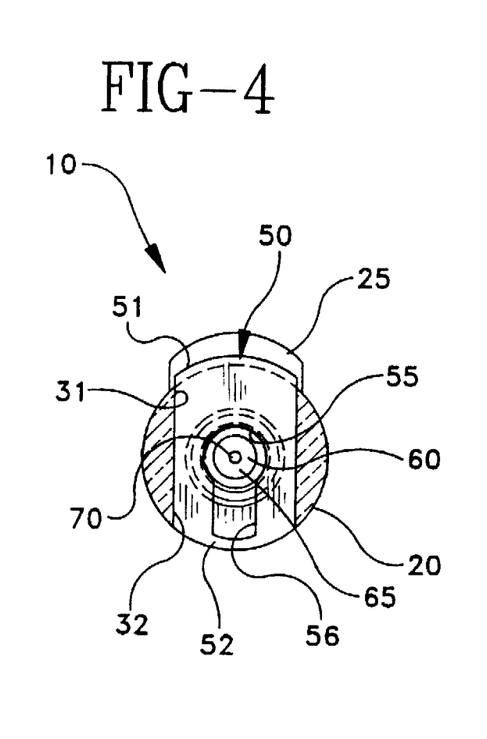
FIG. 4 is a like view but taken along the lines 4—4 of FIG. 2 and so showing the needle retracted.

As in use of the Kulli device, the practitioner is able to retract the needle 70 to a safety or retracted position such as shown in FIGS. 2 and 4 by operating the trigger 50—that is to say, by forcing the lock slider/trigger 50 downward (as drawn) to bring the circular, larger-transverse-dimension portion 55 of the keyhole aperture 52 once again into alignment with the front end 65 of the needle carriage 60 as shown in FIG. 4. (The trigger guard 25 helps avoid inadvertent premature operation of the trigger.)

The larger-dimension portion 55 of the aperture 52, as noted earlier, is big enough for passage therethrough of the front end 65 of the carriage 60; therefore in this juxtaposition of the parts the locking action of the slider 50 upon the carriage 60 is released, no longer opposing the restoring force of the spring 80. In consequence the spring accelerates the needle carriage 60 rearward through the passage 24 of the handle housing 20—to the position shown in FIG. 2.

In that position the entirety of the needle 70, including the piercing point 73, is withdrawn into the interior of the frontal housing 30 and thus is no longer able to puncture the skin of the practitioner or anyone else. The end plug 85 blocks movement of the carriage 60 through the aperture at the rear end 22 of the handle housing 20 and so keeps the carriage 60 and needle 70 within the handle.

Importantly with respect to the present invention, the retracting rearward flight of the needle moves air quickly through the passage 24 of the hollow handle 20. By virtue of openings in the grill 86 and the air-leakage path forward around the needle carrier block, however, retraction develops relatively little air pressure increase within the passage 24.

To the extent that retraction may produce a brief pressure pulse in the passage 24, the filter acts essentially as an air-impermeable wall or piston tending to isolate the interior of the flash chamber 61 from such pressure. In consequence any piston-effect pressure developed during retraction is not applied to the blood in the flash chamber 61, and that blood is not expelled forward and outward through the hollow needle but rather is safely retained within the chamber.

The small lateral port 27 through the cylindrical wall 21 of the handle housing 20 facilitates introduction of a small quantity of viscous material, such as lubricant, into the interior of the passage 24. This viscous material provides the desired energy absorption mentioned earlier.

By virtue of this energy absorbing, a relatively strong spring 80 or other biasing element may be employed for reliable retraction—but without incurring undesirably loud or violent operation in some production units whose manufacturing tolerances aggregate toward maximum retraction speed. In this regard it has been found particularly satisfactory to use a spring that exercises a force in the range of 33 to 40 Newtons per meter (3 to 3.6 ounces per inch) of compression from its relaxed position.

A nominal or ideal value is roughly 37 N/m (3.3 oz/in) —amounting to a nominal 2.2N (8 oz) at 6.1 cm (2.4 inch) compression. The viscous material may be a lubricant such as "High Vacuum Grease" available from the Dow Corning Company.

Merely for purposes of placing these values within the environment of a practical device, and not to limit the scope of the invention as claimed, it is preferred to use these dimensions:

8.6 cm (3.4 inch) length from the rear end of the handle to forward surface of the frontal housing;

5.1 cm (2.0 inch) length from the forward surface of the frontal housing to the tip of the needle;

1.1 cm (0.42 inch) outside diameter of the frontal housing;

0.8 cm (0.30 inch) outside diameter of the handle grip surface;

0.46 cm (0.18 inch) inside diameter of the handle bore near the trigger, with fabrication tolerance of ±0.005 cm (±0.002 inch);

3.0 cm (1.18 inch) overall length of the carrier block;

0.94 cm (0.37 inch) effective length of the segment of the carrier block over which the spring is coiled;

0.33 cm (0.13 inch) outside diameter of that same segment of the carrier block, with fabrication tolerance of ±0.0025 cm (±0.001 inch);

1.8 cm (0.72 inch) length of the remainder of the carrier block—that is, the exterior length of the flash-chamber segment;

1.7 cm (0.67 inch) interior length of the flash chamber;

0.44 cm (0.175 inch) outside diameter of the flash chamber;

0.32 cm (0.125 inch) inside diameter of the flash chamber; and 0.22 cm (0.085 inch) inside diameter of the lubrication port.

For satisfactory operation it is also important to avoid underfilling, overfilling or misfilling the device. Underfilling tends to lead to inadequate energy-absorbing effect, and overfilling tends to make the effect excessive—or, in other words, to render retraction unreliable or possibly, in extreme cases, even to consistently prevent retraction.

To avoid such adverse phenomena the lubricant introduction techniques should be carefully developed to ensure that the lubricant is reasonably well distributed about the needle carrier block and in particular fills the region of the spring coils—but does not extend much rearward along the flash chamber 61. Grease must be kept away from the open rearward end of the needle lumen.

It has not been attempted to measure the speed of retraction or the jerk applied to the handle (and thereby to the hand of the operator) with vs. without the lubricant. Rather, the criteria used for success of the lubricant energy-absorbing technique of the invention have been the satisfaction with and acceptance of the operation by medical personnel.

By those criteria this energy-absorbing technique of the invention has been found to be a total success. In particular it has been found that the invention not only avoids startling or annoying operators, but goes further to convey an operational perception, sensation or so-called "feel" that is very solid, positive and professional—and accordingly enhances significantly the acceptance of the device in the field. Furthermore, no significant variation in at least these perceptions was noted as among different production units.

Figure 5:
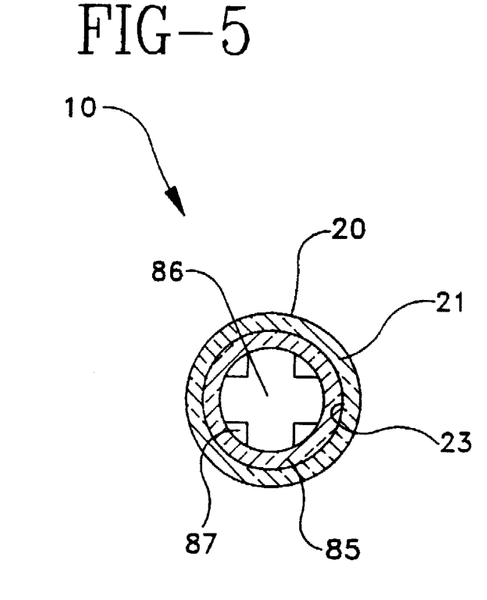
FIG. 5 is a cross-section of the same device taken along the lines 5—5 in either FIG. 1 or 2, and showing an embodiment of the invention that employs for abuse deterrence a grill supported across the interior of the hollow handle to render difficult any access to the needle for forward resetting.

A grill 86 supported within the end plug 70 is provided to frustrate attempts to redeploy the needle 70 (as by inserting a screwdriver, paperclip or like tool to push the needle forward) for reuse. The grill 86 may be cruciform as illustrated, but other adequately strong grill patterns that significantly deter insertion of such tools will serve equally well.

Some prospective reusers may be so determined that they use cutting tools or breaking techniques for access to the needle; accordingly, complete prevention of discarded-device abuse may not be physically possible. Some device configurations, however, such as the grill 86 illustrated, do protect at least against more ordinary efforts such as insertion of pushing tools.

Although it is preferable to use as the receiving and retaining means a movable interior chamber 61 and associated filter 62 as in FIG. 1, alternative means as mentioned earlier may be employed instead. For example, flash blood may be received from within the hollow needle 170 (FIG. 6) and reliably retained, during and after retracting of the needle, in a chamber 161 that is associated with, fixed to, or even integral with the handle housing 120.

Figure 6:
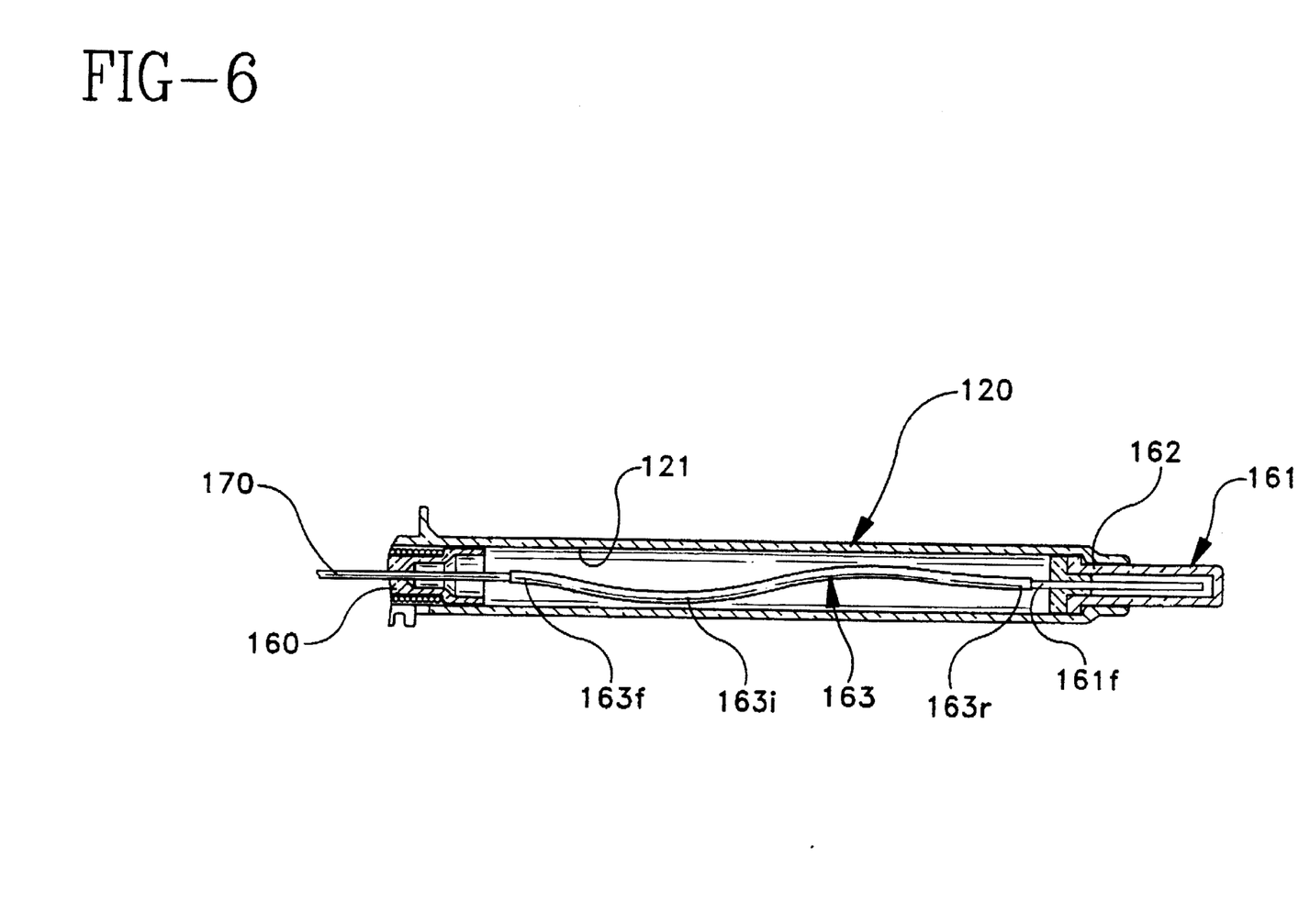
FIG. 6 is a somewhat schematic partial longitudinal section of an alternative embodiment employing for pressure isolation a flexible interconnecting tube, and for abuse deterrence a generally complete obstruction of the interior of the hollow handle.

In such a configuration it is appropriate to provide some means for transmitting blood from within the hollow needle into the chamber, substantially without transmitting into the chamber the compressive force that is developed in the course of retraction. Such a transmitting means may take the form of a flexible tube 163 that interconnects for fluid communication the interior of the flash chamber 161 with the needle lumen.

During retraction the forward end 163f of the flexible tube 163 moves with the needle while the rearward end 163r of the same tube 163 remains fixed to a tubular extension 161f at the front end of the chamber 161 and thus to the handle housing 120. The intervening long segment 163i of the tube 163 takes up the differential motion by bodily deformation.

To facilitate this operation the intervening portion 163i of the tube may if desired be coiled slightly as shown, to facilitate an orderly arrangement of that portion 163i during retraction. This may help avoid its obstructing the advancing needle carriage 160—as for example by tangling, or catching between the advancing needle carriage 160 and the interior bore of the cylindrical handle wall 121. A slightly longer handle 121 is preferred to accommodate the coiled tube 163 after retraction. During flash acquisition, air is exhausted at the rear of the assembly through, for example, a lateral port 162 as in other fixed-flash-chamber devices.

Conceptually somewhat related to the receiving and retaining system of FIG. 6 is a likewise flexible element 262 (FIG. 7) that operates by resilient deformation to take up dimensional differences—but here these are differences between pre- and postflash dimensions, rather than pre- and postretraction dimensions. In this case the flexible element is a translucent or transparent balloon 262 that serves as the flash chamber.

Figure 7:
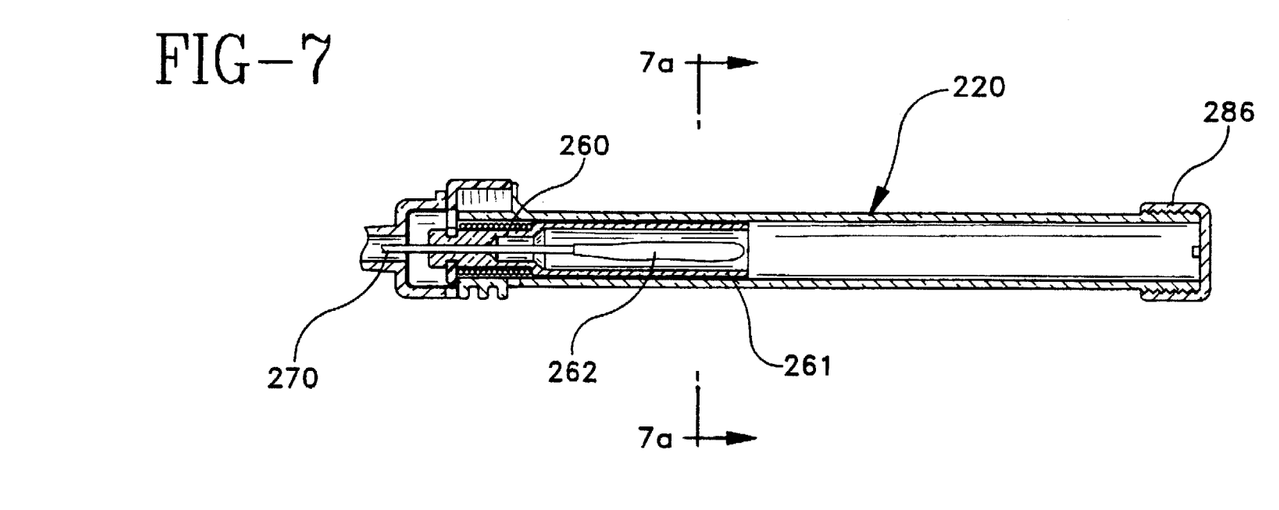
FIGS. 7 and 7a (taken along line 7a—7a in FIG. 7) represent a like schematic section of still another alternative embodiment—employing for pressure isolation an initially flattened, preferably transparent or translucent balloon fixed for liquid communication to the rear of the needle and for energy absorbing a separate laterally biased element, and for abuse deterrence a labyrinthine end cap that similarly provides essentially complete obstruction of the interior of the hollow handle.

The balloon chamber 262 is initially flattened, thus enclosing very little air, and expands with introduction of flash blood through the needle 270—thereby eliminating the need for a selective filter, vent system or the like for exhaust of displaced air and retention of blood. Upon retraction the balloon chamber 262 is protected against potentially compressive forces within the handle 220 by a relatively stiffer plastic sleeve 261.

As can be seen, this FIG. 7 embodiment is also to an extent conceptually related to that of FIGS. 1 through 5, in that the balloon chamber 262 and sleeve 261 during retraction move with the needle. Other forms of receiving and retaining means within the scope of our invention may be seen as related instead to the system of FIG. 6 in that a chamber is associated with the handle housing rather than with the needle—and a filter or vent system accommodates air exhaust ahead of the flash—but no flexible member is used to accommodate dimensional changes.

Figure 8:
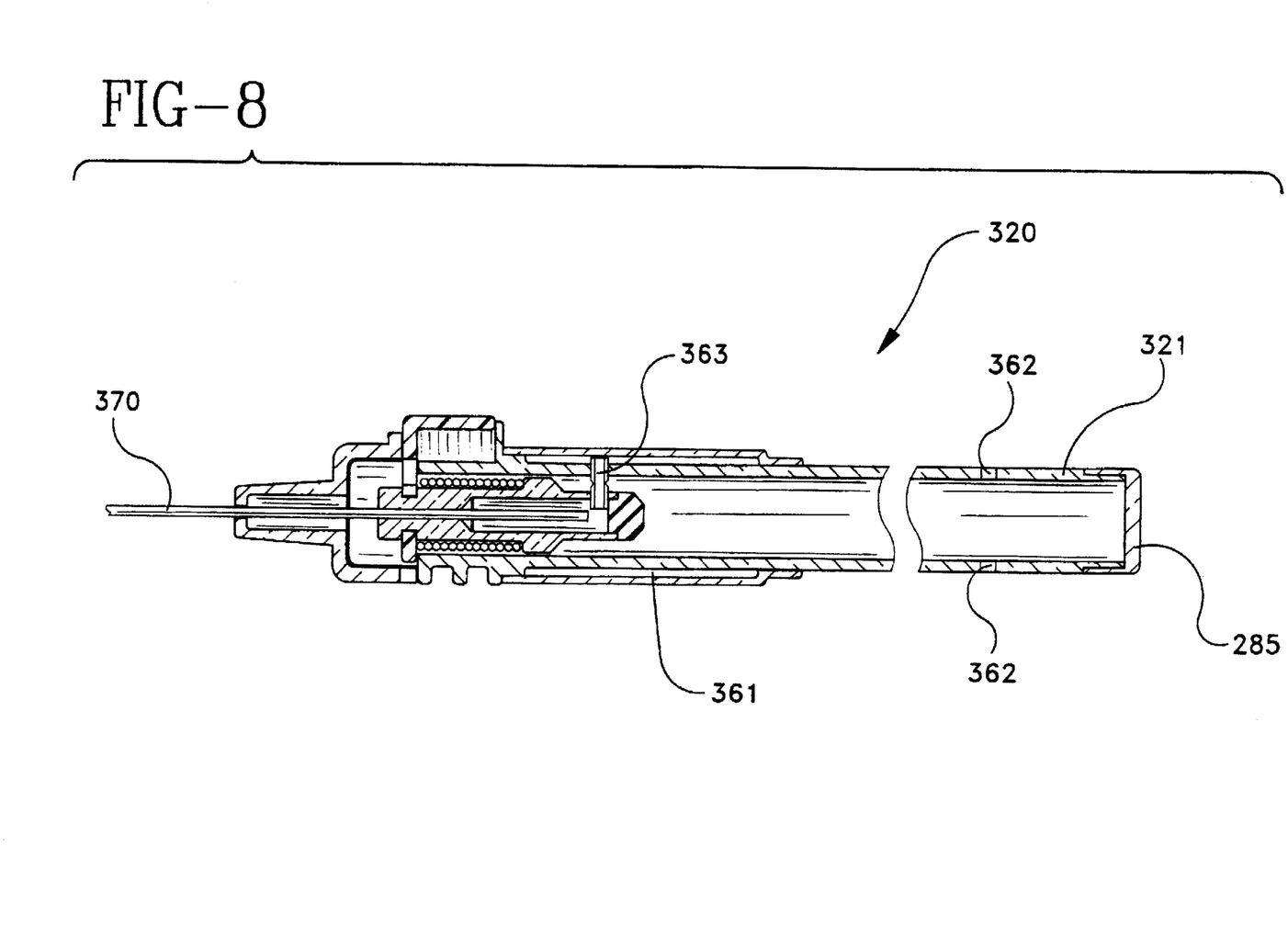
FIG. 8 is a like schematic section of another alternative embodiment employing for pressure isolation a frangible passage and for abuse deterrence a laterally formed piston-pressure relief port that renders difficult any access to the needle for resetting.

For example, one of such other forms employs instead a frangible duct 363 (FIG. 8) for directing flash blood from the needle 370 lumen to a flash chamber 361 fixed to or integral with the handle 320—as for example an annularly arranged chamber 361. In retraction the breakaway duct 363 is left loose within the handle 320.

Another of such forms employs a pivoted flapper-style valve 463 connected to the needle-carriage 460 (FIG. 9) for admitting flash blood from the needle 470 lumen directly to the interior of the passage 424 within the hollow handle 420—and for blocking return passage of that blood from the passage 424 into the lumen in retraction.

Figure 1A:
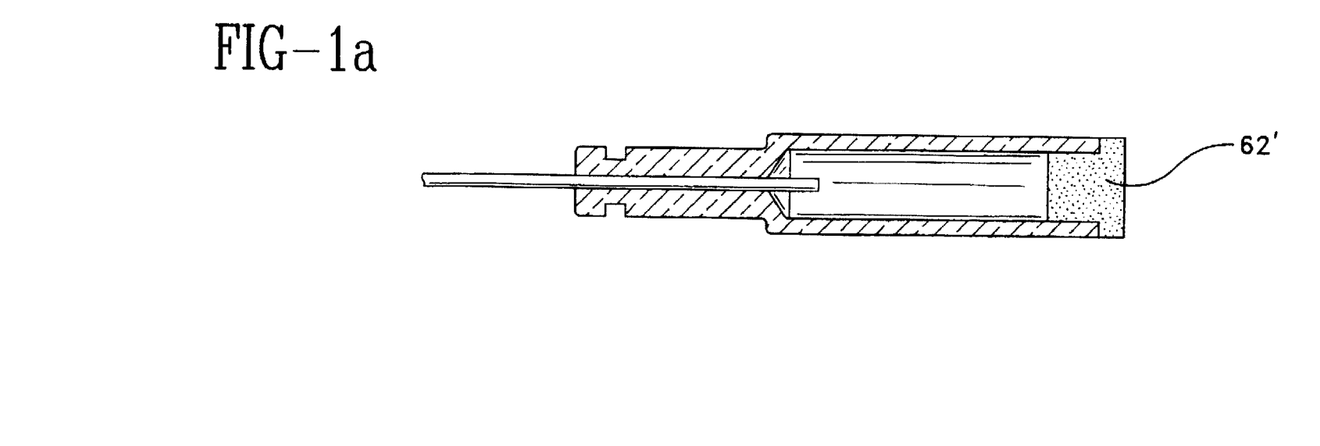
FIG. 1a is a partial like section, enlarged, showing an alternative, crushable energy absorber mounted to the chamber.

Other forms of energy-absorbing means too are, analogously, within the scope of the invention. For instance a crushable element—such as a crushable type of filter 62' (FIG. 1a)—at the rear of the flash chamber may be substituted for the hydrophilic or like filter discussed earlier. The crushable filter may be for instance a sintered plastic unit commercially available from the Porex Company. Alternatively a crushable element in the form of fine molded vanes or the like may be used instead.

Another usable energy absorber is a separate bearing element 227 (FIGS. 7, 7a) may be fixed to the needle—preferably carried in the needle carriage 260—and biased laterally (e.g., radially outward) as by a crescent spring 227s against the interior cylindrical surface 221 of the hollow handle housing 220.

Figure 7A:
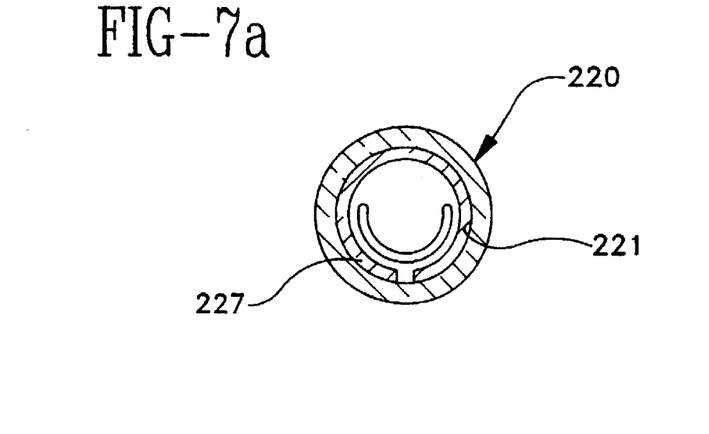

Also available is the converse system—that is to say, a separate bearing element (not illustrated) carried in the inner cylindrical surface 221 of the housing 220 and bearing against a surface fixed to the needle—preferably carried on the carriage 260. Either of these biased-element systems is believed to provide drag or damping as desired.

Yet another form of energy-absorbing means is a dashpot piston 427 (FIG. 9) fixed at the end of the needle for developing damping, during retraction, through friction with liquid—and more specifically the flash blood—inside the hollow handle 420. For manufacturing convenience this dashpot element 427 is advantageously integrated with the check valve 463 discussed earlier.

Other forms of redeployment-deterring means too are within the scope of the invention. For example the two end walls of a flash chamber 161 (FIG. 6) that is firmly fixed to the rear of the hollow handle 120 also form a complete obstruction of the hollow handle 120—thus deterring insertion of a tool through that rear portion of the handle to redeploy the needle 170. This would remain essentially true even if a puncturable filter, forming the rear of the chamber, were provided in place of the lateral port 162—as the forward wall of the chamber would still provide a near-complete barrier.

As another example, a labyrinthine end plug 286 (FIG. 7) can serve to exhaust air from the internal passage 221 of the handle housing 220, while entirely blocking insertion of a tool into the housing 220 to redeploy the needle. Alternatively air exhaust can be effected through relief ports 362 (FIG. 8) formed laterally, e.g., radially, through the cylindrical wall 321 of the handle housing 320—rather than longitudinally at the end of the housing 320—thereby permitting use of an entirely solid endcap 285 to obstruct tool insertion.

Still further, abuse-deterring means may take the form of a ratchet element 486a (FIG. 9), cooperating with the narrow portion 56 (FIG. 4) of the keyhole aperture in the lock slider/trigger 450, to prevent resetting of the trigger 450 after the assembly has been first made ready for use. As will be understood the mechanism must permit resetting of the trigger 450 one initial time, since this is the procedure by which the needle is deployed initially for its intended use.

Figure 9:
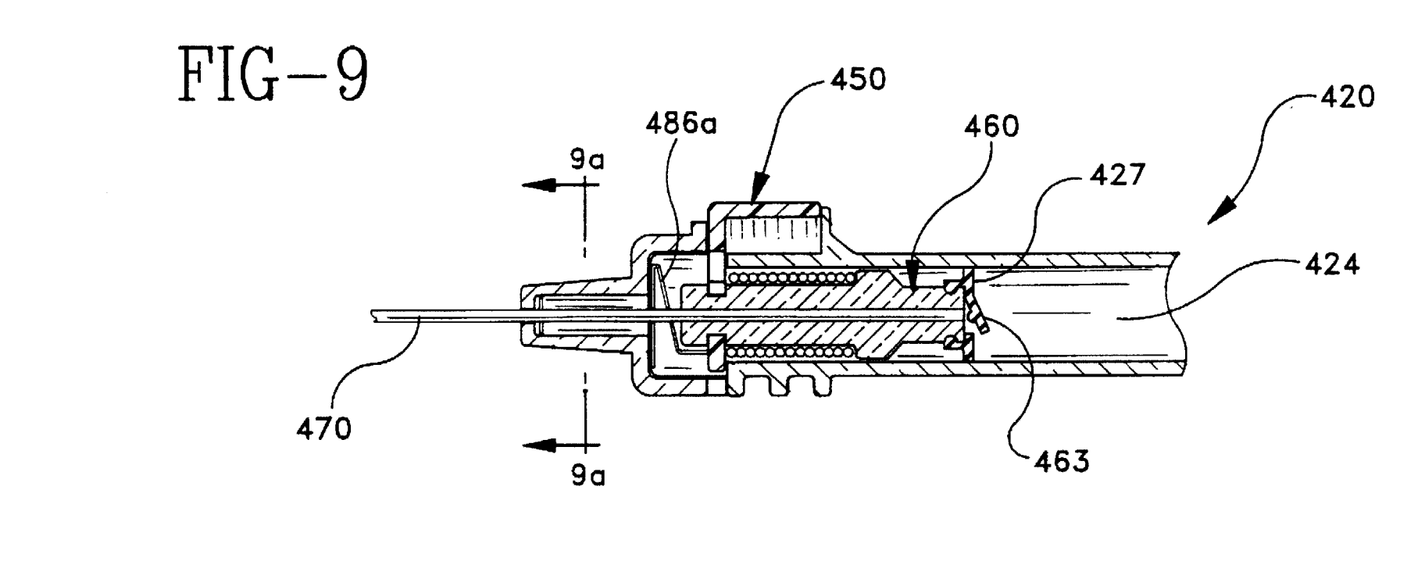
FIGS. 9 and 9a (greatly enlarged) are like schematic sections of yet another alternative embodiment—employing for pressure isolation a check valve, for energy absorbing a dashpot member that is integrated with the valve, and for abuse deterrence ratchet elements to prevent, respectively, forward motion of the needle and reengagement of the trigger to its locking position.
Figure 9A:
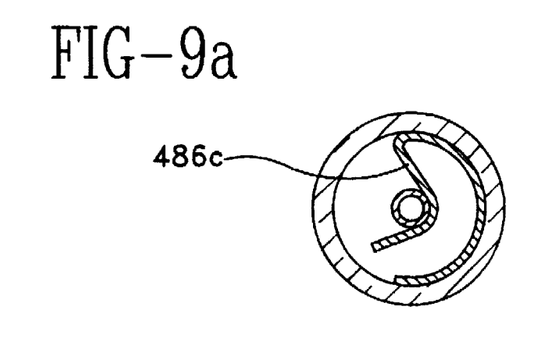

Analogously, further abuse-deterring means may take the form of a ratchet-like element 486c which upon retraction falls in front of the needle 470 piercing end, to block subsequent forward movement of the needle.

It will be understood that the foregoing disclosure is intended to be merely exemplary, and not to limit the scope of the invention—which is to be determined by reference to the appended claims.

What is claimed is:

1. An introducer needle assembly, comprising:

a hollow needle having a proximal end and a sharp distal end;

a hollow handle having a proximal end and a distal end;

a needle hub connected to the proximal end of the hollow needle and slidably disposed in the hollow handle;

a spring operably connected to the needle hub;

a latch operably engaging the needle hub selectively to maintain the needle hub adjacent to the distal end of the hollow handle against the bias of the spring; and a flashback chamber fixedly connected to the hollow handle so the needle and the needle hub are movable with respect to the flashback chamber and the flashback chamber is in fluid communication with the hollow needle for receiving blood from within the hollow needle and wherein the flashback chamber does not move with respect to the hollow handle when the needle hub is moved proximally in the hollow handle.

2. The introducer needle assembly of claim 1 wherein the flashback chamber is adjacent to the proximal end of the hollow handle and a flexible tube connects the hollow needle to the flashback chamber.

3. The introducer needle assembly of claim 1 wherein the flashback chamber is adjacent to the distal end of the hollow handle and a frangible tube connects the hollow needle to the flashback chamber.

4. An introducer needle assembly, comprising:

a hollow needle having a proximal end and a sharp distal end;

a hollow handle having a proximal end and a distal end;

a needle hub connected to the proximal end of the hollow needle and slidably disposed in the hollow handle;

a spring operably connected to the needle hub;

a latch operably engaging the needle hub selectively to maintain the needle hub adjacent to the distal end of the hollow handle against the bias of the spring; and an expandable balloon flashback chamber in fluid communication with the hollow needle for receiving blood from within the hollow needle and wherein the expandable balloon flashback chamber has a volume that increases when increasing amounts of blood are received therein and does not require any mechanism for venting air therefrom.

5. The introducer needle assembly of claim 4 further comprising a stiff sleeve member extending from the needle hub alongside the expandable flashback chamber.

* * * * *